United States Patent
Sewall et al.

(10) Patent No.: US 7,816,341 B2
(45) Date of Patent: Oct. 19, 2010

(54) HOMOGENEOUS, THERMOREVERSIBLE GEL CONTAINING REDUCED VISCOSITY CARRAGEENAN AND PRODUCTS MADE THEREFROM

(75) Inventors: Christopher J. Sewall, Hope, ME (US); Peter J. Riley, Yardley, PA (US); William R. Blakemore, Topsham, ME (US)

(73) Assignee: FMC Corporation, Philadelphia, PA (US)

(*) Notice: Subject to any disclaimer, the term of this patent is extended or adjusted under 35 U.S.C. 154(b) by 0 days.

(21) Appl. No.: 10/824,688

(22) Filed: Apr. 14, 2004

(65) Prior Publication Data

US 2005/0014852 A1   Jan. 20, 2005

Related U.S. Application Data

(60) Provisional application No. 60/462,785, filed on Apr. 14, 2003, provisional application No. 60/462,721, filed on Apr. 14, 2003, provisional application No. 60/462,758, filed on Apr. 14, 2003, provisional application No. 60/462,617, filed on Apr. 14, 2003, provisional application No. 60/462,793, filed on Apr. 14, 2003, provisional application No. 60/462,783, filed on Apr. 14, 2003, provisional application No. 60/462,792, filed on Apr. 14, 2003, provisional application No. 60/462,794, filed on Apr. 14, 2003.

(51) Int. Cl.
  A61K 31/715 (2006.01)
  A61K 47/00 (2006.01)
  A61K 9/48 (2006.01)
(52) U.S. Cl. .................... 514/54; 514/944; 424/451
(58) Field of Classification Search .............. 514/54, 514/944; 424/451
  See application file for complete search history.

(56) References Cited

U.S. PATENT DOCUMENTS

| | | |
|---|---|---|
| 348,669 A | 9/1886 | Gruber |
| 2,802,000 A | 8/1957 | Caldwell et al. |
| 2,813,093 A | 11/1957 | Caldwell et al. |
| 2,825,727 A | 3/1958 | Caldwell |
| 2,876,217 A | 3/1959 | Paschall |
| 3,058,827 A | 10/1962 | Graham |
| 3,094,517 A | 6/1963 | Stanley |
| 3,176,003 A | 3/1965 | Stancioff |
| 3,329,509 A | 7/1967 | Julius |
| 3,378,546 A | 4/1968 | Tsuzuki |
| 3,460,717 A | 8/1969 | Thomas |
| 3,499,962 A | 3/1970 | Warzburg et al. |
| 3,505,110 A | 4/1970 | Kesler et al. |
| 3,607,394 A | 9/1971 | Germino et al. |
| 3,849,395 A | 11/1974 | Moirano |
| 3,865,603 A | 2/1975 | Szymanski et al. |
| 3,956,173 A | 5/1976 | Towle |
| 3,962,482 A | 6/1976 | Comer et al. |
| 4,009,291 A | 2/1977 | Mitchell et al. |
| 4,026,986 A | 5/1977 | Christen et al. |
| 4,096,327 A | 6/1978 | Guiseley |
| 4,129,134 A | 12/1978 | Hind et al. |
| 4,231,803 A | 11/1980 | Bovier et al. |
| 4,276,320 A | 6/1981 | Moirano |
| 4,443,486 A | 4/1984 | Guiseley |
| 4,600,439 A | 7/1986 | Schneider et al. |
| 4,615,897 A | 10/1986 | Brown et al. |
| 4,626,288 A | 12/1986 | Trzasko et al. |
| 4,632,848 A | 12/1986 | Gassett et al. |
| 4,643,894 A | 2/1987 | Porter et al. |
| 4,725,441 A | 2/1988 | Porter |
| 4,738,724 A | 4/1988 | Wittwer et al. |
| 4,795,642 A | 1/1989 | Cohen et al. |
| 4,828,841 A | 5/1989 | Porter |
| 4,851,394 A | 7/1989 | Kubodera |
| 4,935,243 A | 6/1990 | Borkan et al. |
| 5,002,934 A | 3/1991 | Norton et al. |
| 5,051,304 A | 9/1991 | David et al. |
| 5,089,307 A | 2/1992 | Ninomiya et al. |
| 5,146,730 A | 9/1992 | Sadek et al. |

(Continued)

FOREIGN PATENT DOCUMENTS

EP   0 169 319   1/1986

(Continued)

OTHER PUBLICATIONS

Informe Technico 26, Macroalgas De Interes Comercial En Las Costas Del Sur De Chubut Y Norte De Santa Cruz, Maria Lutz Piriz y Graciela Casas, ISSN No. 0328-462X, 1996. pp. (34). (Partial Translation).

(Continued)

*Primary Examiner*—Shaojia Anna Jiang
*Assistant Examiner*—Everett White (57) ABSTRACT

The present invention is directed to a homogeneous, thermoreversible gel comprising carrageenan wherein the carrageenan has a viscosity of less than 10 cP at 75° C. when measured in a 0.10 molar aqueous sodium chloride solution containing 1.5% by weight of the carrageenan based on the weight of all components in the solution, and optionally at least one of a plasticizer, a second film former, a bulking agent, and a pH controlling agent, wherein the gel has a solids content of at least 40%. The present invention is also directed to processes for the preparation thereof, as well as to variety of products containing the gel including edible products, soft capsules, hard capsules and solid forms encapsulating powders, tablets, caplets, etc.

24 Claims, 5 Drawing Sheets

U.S. PATENT DOCUMENTS

| | | |
|---|---|---|
| 5,224,989 A | 7/1993 | Likarova |
| 5,264,223 A | 11/1993 | Yamamoto et al. |
| 5,334,640 A | 8/1994 | Desai et al. |
| 5,342,626 A | 8/1994 | Winston, Jr. et al. |
| 5,422,134 A | 6/1995 | Hart et al. |
| 5,431,917 A | 7/1995 | Yamamoto et al. |
| 5,451,673 A | 9/1995 | Fishman et al. |
| 5,484,598 A | 1/1996 | Schurig et al. |
| 5,525,368 A | 6/1996 | Rha et al. |
| 5,549,983 A | 8/1996 | Yamanis |
| 5,550,178 A | 8/1996 | Desai et al. |
| 5,554,385 A | 9/1996 | Stroud |
| 5,569,466 A | 10/1996 | Tanner et al. |
| 5,587,412 A | 12/1996 | Borchers et al. |
| 5,614,217 A | 3/1997 | Chiprich et al. |
| 5,620,757 A | 4/1997 | Ninomiya et al. |
| 5,646,206 A | 7/1997 | Coffin et al. |
| 5,656,294 A | 8/1997 | Friend et al. |
| 5,672,699 A | 9/1997 | Billmers et al. |
| 5,726,008 A | 3/1998 | Maskasky |
| 5,756,123 A | 5/1998 | Yamamoto et al. |
| 5,804,243 A | 9/1998 | Loh et al. |
| 5,811,388 A | 9/1998 | Friend et al. |
| 5,817,323 A | 10/1998 | Hutchinson et al. |
| 5,820,259 A | 10/1998 | Cummins et al. |
| 5,932,639 A | 8/1999 | Eden et al. |
| 5,976,586 A | 11/1999 | Feller |
| 6,030,641 A | 2/2000 | Yamashita et al. |
| 6,063,915 A | 5/2000 | Hansen et al. |
| 6,066,368 A | 5/2000 | Billmers et al. |
| 6,099,876 A | 8/2000 | Nussinovitch |
| 6,143,324 A | 11/2000 | Michaud et al. |
| 6,146,570 A | 11/2000 | Stern |
| 6,210,709 B1 | 4/2001 | Laba et al. |
| 6,214,376 B1 | 4/2001 | Gennadios |
| 6,326,028 B1 | 12/2001 | Nivaggioli et al. |
| 6,331,205 B1 | 12/2001 | Paris et al. |
| 6,340,473 B1 | 1/2002 | Tanner et al. |
| 6,375,981 B1 | 4/2002 | Gilleland et al. |
| 6,387,354 B1 | 5/2002 | Bixler et al. |
| 6,432,448 B1 | 8/2002 | Augello et al. |
| 6,447,755 B1 | 9/2002 | Ballard |
| 6,479,649 B1 | 11/2002 | Tsai et al. |
| 6,497,887 B1 | 12/2002 | Zecchino et al. |
| 6,517,865 B2 | 2/2003 | Cade et al. |
| 6,528,088 B1 | 3/2003 | Gilleland et al. |
| 6,582,727 B2 | 6/2003 | Tanner et al. |
| 6,607,748 B1 | 8/2003 | Lenaerts et al. |
| 6,635,275 B1 | 10/2003 | Scott et al. |
| 6,649,188 B2 | 11/2003 | Gilleland et al. |
| 6,790,495 B1 | 9/2004 | Tomka et al. |
| 6,949,256 B2 | 9/2005 | Fonkwe et al. |
| 6,967,037 B1 * | 11/2005 | Jønsson et al. ............. 426/548 |
| 2002/0081331 A1 | 6/2002 | Tanner et al. |
| 2002/0122822 A1 | 9/2002 | Bunick et al. |
| 2002/0142031 A1 | 10/2002 | Gilleland et al. |
| 2002/0176317 A1 | 11/2002 | Bellasalma et al. |
| 2003/0084641 A1 | 5/2003 | Tanner et al. |
| 2003/0085487 A1 | 5/2003 | Tanner et al. |
| 2003/0138482 A1 | 7/2003 | Fonkwe et al. |
| 2003/0211146 A1 | 11/2003 | Scott et al. |
| 2004/0013723 A1 | 1/2004 | Parikh et al. |
| 2004/0052839 A1 | 3/2004 | Archibald et al. |
| 2004/0087669 A1 | 5/2004 | Hausmanns et al. |
| 2004/0180083 A1 | 9/2004 | Shiraishi et al. |
| 2004/0192907 A1* | 9/2004 | Resch et al. ............. 536/123 |
| 2005/0008677 A1 | 1/2005 | Modliszewski et al. |
| 2005/0013847 A1 | 1/2005 | Ballard et al. |
| 2005/0014852 A1 | 1/2005 | Sewall et al. |
| 2005/0019294 A1 | 1/2005 | Modliszewski et al. |
| 2005/0019295 A1 | 1/2005 | Ballard et al. |
| 2005/0048185 A1 | 3/2005 | Ballard et al. |
| 2005/0069579 A1 | 3/2005 | Kamaguchi et al. |
| 2005/0070703 A1 | 3/2005 | Muller et al. |
| 2005/0089548 A1 | 4/2005 | Virgalitto et al. |
| 2005/0163833 A1 | 7/2005 | Muller |

FOREIGN PATENT DOCUMENTS

| | | |
|---|---|---|
| EP | 0 400 484 | 12/1990 |
| EP | 0 408 503 | 1/1991 |
| EP | 0 409 781 | 1/1991 |
| EP | 0 409 782 | 1/1991 |
| EP | 0 409 788 | 1/1991 |
| EP | 0 471 558 | 2/1992 |
| EP | 0 547 551 | 6/1993 |
| EP | 0 606 486 | 7/1994 |
| EP | 0 622 408 | 11/1994 |
| EP | 0 633 896 | 1/1995 |
| EP | 0 714 656 A1 | 6/1996 |
| EP | 0 761 691 | 3/1997 |
| EP | 1297827 A2 | 4/2003 |
| JP | 60-55039 | 3/1985 |
| JP | 60088047 A | 5/1985 |
| JP | 61 10508 A | 1/1986 |
| JP | 62-186754 | 8/1987 |
| JP | 63-164858 | 7/1988 |
| JP | 01-143827 | 6/1989 |
| JP | 3-12231 | 1/1991 |
| JP | 3-53873 | 3/1991 |
| JP | 05-43471 | 2/1993 |
| JP | 09-25228 | 1/1997 |
| JP | 2000125801 A | 5/2000 |
| JP | 2001-39863 | 2/2001 |
| JP | 2003-504326 | 2/2003 |
| JP | 2003-299714 | 10/2003 |
| JP | 2004-167084 | 6/2004 |
| JP | 2005-508359 | 3/2005 |
| JP | 2005-112849 | 4/2005 |
| JP | 2005-513255 | 5/2005 |
| SU | 352444 A | 10/1972 |
| WO | WO 94/25493 | 11/1994 |
| WO | WO 97/49762 | 12/1997 |
| WO | WO 98/20860 | 5/1998 |
| WO | WO 99/07347 | 2/1999 |
| WO | WO 00/10538 | 3/2000 |
| WO | WO 00/18835 | 4/2000 |
| WO | WO 00/36930 | 6/2000 |
| WO | WO-01/03677 | 1/2001 |
| WO | WO 01/37817 | 5/2001 |
| WO | WO 01/91721 | 12/2001 |
| WO | WO 01/92400 | 12/2001 |
| WO | WO 01/92401 | 12/2001 |
| WO | WO-02/43657 A2 | 6/2002 |
| WO | WO 03/009832 | 2/2003 |
| WO | WO-03/035044 | 5/2003 |

OTHER PUBLICATIONS

Seasonal variation of carrageenans in tetrasporic, cystocarpic and 'sterile' stages of *Gigartina skottsbergii* S.et G. (Rhodophyta, *Gigartinales* ), (Piriz & Cerezo) Hydrobiologia 226: 65-69, 1991, Kluwer Academic Publishers. Printed in Belgium.

Painter et al. Fundamentals of Polymer Science. Lancaster: Technomic Publishing 1994 p. 15.

FMC Corporation Marine Colloids Division Application Bulletin G-39 "Water-Gelling Properties of Carrageenan" p. 1 to p. 16, Jun. 1990.

"Water Gelling Applications of Carrageenan", FMC Corporation, Springfield, NJ (1981).

F. Sedlmeyer, et al. "Influence of the Composition of milk-protein k/l-hybrid-carrageenan gels on product properties", Colloids and Surfaces B: Biointerfaces, (2003), vol. 31, pp. 13-20.

Eleya, et al., "Rheology of k-carrageenan and B-lactoglobulin mixed gels", Food Hydrocolloids, vol. 14, pp. 29-40, 2000.

Falshaw et al., "Structure and performance of commercial kappa-2 carrageenan extracts I. Structure analysis", , Food Hydrocolloids, vol. 15, pp. 441-452; 2001.

Villanueva et al., "Structure and functional performance of gigartinacean kappa-iota hydrid carrageenan and solieriacean kappa-iota carrageenan blends", Food Hydrocolloids. vol. 18, pp. 283-292; 2004.

Bixler et al., "Kappa-2 carrageenan: structure and performance of commercial extracts II. Performance in two simulated dairy application", Food Hydrocolloids, vol. 15, pp. 619-630; 2001.

van de Velde et al., "On the structure of k/i-hybrid carrageenans", Carbohydrate Research, vol. 331, pp. 271-283, 2001.

C. Rochas et al., "Role of the Molecular Weight on the Mechanical Properties of Kappa Carrageenan Gels", Carbohydrate Polymers, vol. 12, pp. 255-566, 1990.

de Vries J., "Interaction of carrageenan with other ingredients in dairy dessert gels", Gums and stabilisers for the food industry 11: proceedings of the 11th conference, Wrexham, vol. 11 (2002), No. -, pp. 201-210, Jul. 2001.

R. Falshaw et al., "Structure and performance of commercial K-2 carrageenan extracts", Food Hydrocolloids, vol. 17, pp. 129-139, 2003.

FMC BioPolymer, "Carrageenan Matrices for Entrapment", Issue No. 1, Apr. 1993.

Henry J. Witt, "Carrageenan Nature's Most Versatile Hydrocolloid", pp. 347-360, 1985.

Glicksman, M., "Gum Technology in the Food Industry", Academic Press, pp. 213-228, 1969.

C. J. Lawson et al., "Carrageenans", J.C.S. Perkin I, pp. 2177-2182, 1973.

H. J. Bixler, "Recent developments in manufacturing and marketing carrageenan", Hydrobiologia, pp. 35-57, 1996.

M. C. Matulewicz et al., "Carrageenan Systems from Tetrasporic or Cystocarpic Stages of *Gigartina Skottsbergii*", Phytochemistry, vol. 28, pp. 2937-2941, 1989.

M. C. Matulewicz et al., "Methylation Analysis of Carrageenans from Tetrasporic and Cystocarpic Stages of *Gigartina Skottsbergii*", Phytochemistry, vol. 29, No. 11, pp. 3407-3410, 1990.

C. Rochas et al., "Relation Between the Molecular Strcture and Mechanical Properties of Carrageenan Gels", Carbohydrate Polymers, vol. 10, pp. 115-127, 1989.

Stancioff, D. J. And Stanley, N. F., "Infrared and Chemical Studies on Algal Polysaccharides", Prod. Intl. Seaweed Symp. 6, pp. 595-609, 1969.

Bellion, C. et al, Analysis of Kappa-Iota Hybrid Carrageenans with Kappa-Carrageenase, Iota-Carrageenase and $^{13}$C N.M.R., Xth International Seaweed Symposium, Walter de Gruyter & Co., Berlin-New York, pp. 379-384, 1981.

Peats, S., "The Infrared Spectra of Carrageenans Extracted from Various Algae", Xth International Seaweed Symposium, Walter de Gruyter & Co., Berlin-New York, pp. 495-502, 1981.

* cited by examiner

HOMOGENEOUS, THERMOREVERSIBLE GEL CONTAINING REDUCED VISCOSITY CARRAGEENAN AND PRODUCTS MADE THEREFROM

RELATED APPLICATIONS

This application claims the benefit of U.S. Provisional Application Nos. 60/462,785; 60/462,721; 60/462,758; 60/462,617; 60/462,793; 60/462,783; 60/462,792; 60/462,794; all filed on Apr. 14, 2003.

FIELD OF THE INVENTION

The present invention is directed to a homogeneous, thermoreversible gel comprising carrageenan wherein the carrageenan has a viscosity of less than 10 cP at 75° C. when measured in a 0.10 molar aqueous sodium chloride solution containing 1.5% by weight of the carrageenan based on the weight of all components in the solution, and optionally at least one of a plasticizer, a second film former, a bulking agent, and a pH controlling agent, wherein the gel has a solids content of at least 40%. The present invention is also directed to processes for the preparation thereof, as well as to variety of products containing the gel including edible products, soft capsules, hard capsules and solid forms encapsulating powders, tablets, caplets, etc.

BACKGROUND OF THE INVENTION

Carrageenan is a commercially significant galactan polysaccharide found in red seaweed. All carrageenans contain repeating galactose units joined by alternating $\alpha 1 \rightarrow 3$ and $\beta 1 \rightarrow 4$ glycosidic linkages and are sulfated to widely varying degrees. The types of carrageenan may be distinguished, in part, by their degree and position of sulfation, as well as the seaweed from which they are obtained. The various types of carrageenan include kappa, kappa-2, iota, lambda, mu and nu. Because carrageenans vary in their composition and structure, they are known to vary in properties and uses. Carrageenans also vary in molecular weight, cation content and type.

In high solids systems, for example, greater than 40% solids, carrageenan gel forming compositions have been known to create highly viscous systems that create processing problems when the gel is made, e.g., such processing requires significant heat, shear, handling in order to prevent premature gelling or formation of gels and gel films that are less than fully homogeneous (resulting in gels of weaker strength). Important industrial applications, such as the manufacture of soft capsules, hard capsules, edible products (gummies, candies, etc.), solid forms encapsulating powders, tablets, etc., could benefit from the use of particular carrageenan gels that gel at reduced temperatures. It has long been believed that the gelling temperature of carrageenan is independent of its molecular weight. To Applicants' surprise, in high solids carrageenan gels, such as at least 40% solids, the gels and gel films containing reduced molecular weight carrageenans as referenced herein result in a highly desirable lowering of the gelling temperature.

SUMMARY OF THE INVENTION

The present invention is directed to a homogeneous, thermoreversible gel comprising carrageenan wherein the carrageenan has a viscosity of less than 10 cP at 75° C. when measured in a 0.10 molar aqueous sodium chloride solution containing 1.5% by weight of the carrageenan based on the weight of all components in the solution, and optionally at least one of a plasticizer, a second film former, a bulking agent, and a pH controlling agent, wherein the gel has a solids content of at least 40%. The present invention is also directed to processes for the preparation thereof, as well as to variety of products containing the gel including edible products (e.g., gummies, candies), soft capsules, hard capsules and solid forms encapsulating powders, tablets, caplets, etc. The present invention is also directed to a process for lowering the gelling temperature of carrageenan gels and gel films comprising using the reduced molecular weight carrageenan described herein.

DETAILED DESCRIPTION OF THE INVENTION

As noted above, carrageenan is a commercially significant galactan polysaccharide found in red seaweed. The preferred types of carrageenan that may be used in this invention are kappa, kappa-2 and iota carrageenan. These types of carrageenan may be distinguished, in part, by their degree and position of sulphation, as well as the seaweed from which they are obtained. For example, iota carrageenan has a repeating unit of D-galactose-4-sulfate-3,6-anhydro-D-galactose-2-sulfate providing a sulfate ester content of about 25 to 34%. Iota carrageenan can be obtained, for example, from *Eucheuma denticulatum* (also referred to as "*Spinosum*"). Kappa carrageenan has a repeating unit of D-galactose-4-sulfate-3,6-anhydro-D-galactose and is obtained, for example, from *Kappaphycus alvarezii* (also known as "*Eucheuma cottonii*"). In contrast, kappa-2 carrageenan is reported by R. Falshaw, H. J. Bixler and K. Johndro, *Structure and Performance of Commercial Kappa-2 Carrageenan Extracts*, Food Hydrocolloids 15 (2001) 441-452, and by H. Bixler, K Johndro and R Falshaw, *Kappa-2 carrageenan: structure and performance of commercial extracts II*, Food Hydrocolloids 15 (2001) 619-630 to be copolymers containing a certain amount of kappa repeating units (3:6-anhydroglactose (3:6-AG)) and iota repeating units (3:6-anhydrogalactose-2-sulfate (3:6-AG-2-S)) covalently bound in the copolymer backbone and obtained from certain *Gigartinaceae* algae. The foregoing references state that such kappa-2 carrageenans have distinctly different properties as compared to simple mixtures of kappa and iota carrageenans. Other references discussing kappa-2 carrageenan are discussed in these publications. While there has been considerable confusion historically about the physical nature of kappa-2 carrageenans, recent studies, such as those mentioned immediately above, have confirmed that kappa-2 carrageenans are copolymers containing kappa and iota repeating units covalently bound (in certain ratios of kappa to iota moieties) in the copolymer backbone in clear distinction to physical mixtures of kappa and iota polymers.

As used herein, kappa-2 carrageenan has a molar ratio of 3:6 AG-2S to 3:6 AG content of 25 to 50%, iota carrageenan has a molar ratio of 3:6 AG-2S to 3:6 AG content of 80 to 100% and kappa carrageenan has a molar ratio of 3:6 AG-2S to 3:6 AG content less than that for kappa-2 carrageenan. For example, kappa carrageenan from *Eucheuma cottonii*, a commonly known and used seaweed source for kappa carrageenan, has a molar ratio of 3:6 AG2S to 3:6 AG content of less than about 10%; and iota carrageenan from *Spinosum*, a commonly known and used seaweed source for iota carrageenan, has a molar ratio of 3:6 AG2S to 3:6 AG content greater than about 85%. This means that kappa-2 carrageenan comprises a ratio of kappa (3:6-AG) repeating units to iota (3:6-AG-2-S) repeating units between 1.0 to 3.0:1, more particularly, 1.5 to 3.0:1 (more particularly depending on the desired application). The molar ratios of 3:6 AG-2S to 3:6 AG content defined herein hold for iota, kappa and kappa-2 carrageenans regardless of their degree of modification and precursor content (e.g, mu and nu repeating units). Thus, any reduced molecular weight carrageenans meeting the definitions herein, regardless of their degree of modification (from alkali treatment), are within the scope of this invention.

The kappa-2 carrageenan to be used in the present invention may be contained within or purified or separated from a number of seaweed species within the class of, for example, *Gigartinaceae* algae such as *Gigartina radula*, *Gigartina corymbifera*, *Gigartina skottsbergii*, *Iridaea cordata*, *Sarcothalia crispata*, and *Mazzaella laminarioides*. The seaweed source of the kappa-2 carrageenan to be used in this invention is any that produces kappa-2 carrageenan having the molar content of 3:6 AG-2S to 3:6 AG described herein.

Recovery methods of the carrageenans from their sources include the optional full or partial filtration of insolubles from the starting material or the use of unfiltered material, as well as extruded seaweed. It is understood that during the recovery process of the carrageenan from the above seaweeds small or trace amounts of other carrageenans may be present (e.g., lambda carrageenans) and such can be used with the carrageenans in the present invention.

The carrageenan in the gel of the present invention is a reduced molecular weight carrageenan having a viscosity of less than 10 cP, more particularly, 5 to 8 cP, at 75° C. when measured in a 0.10 molar aqueous sodium chloride solution containing 1.5 by weight of the reduced molecular weight carrageenan based on the weight of all components in the solution. This viscosity test can be performed using a Brookfield LVF (Brookfield Engineering Laboratories, Inc.) viscometer using Spindle #1 at 60 r.p.m. and determining the viscosity after six revolutions.

The gels of the invention have a solids content of at least 40%, at least 50%, at least 60%, at least 70%, at least 80% and at least 90% by weight of all components in the gel.

The reduced molecular weight carrageenans used in the gel of the invention generally contain a cation, and that cation can be at least one of calcium, potassium, magnesium, ammonium or sodium cation. Sodium and potassium are preferred for kappa and kappa-2 carrageenan, while sodium, potassium and calcium are preferred for iota carrageenan. The sodium and potassium content, or mixture thereof, for kappa and kappa-2 carrageenan, may be at least 75%, 80%, 85%, 90%, 95% or 98% by weight of the total cation content thereof; and the sodium, potassium and calcium content for the iota carrageenan, or mixture thereof, may be at least 75%, 80%, 85%, 90%, 95% or 98% by weight of the total cation content thereof.

The gels of the present invention using the reduced molecular weight carrageenans described herein have been found to lower the gelling temperature of the resulting gel as compared to carrageenans of similar type and content having a higher molecular weight. For example, Applicants have found that the reduced molecular weight iota carrageenans described herein have reduced the gelling temperature from about 81° C. (iota carrageenan having 3.37% potassium and 1.3% calcium by weight of the carrageenan and a viscosity of 23 cP when measured using the tests herein) to about 34° C. (iota carrageenan of the invention having 3.37% potassium and 1.3% calcium by weight of the carrageenan and a viscosity of 6 cP when measured using the tests herein) and from about 60° C. (iota carrageenan having 7.8% sodium by weight of the carrageenan (0% potassium and calcium) and a viscosity of 23 cP when measured using the tests herein) to about 30° C. (iota carrageenan of the invention having 7.5% sodium and 0.5% potassium by weight of the carrageenan and a viscosity of 6 cP when measured using the tests herein). Applicants have further found that the reduced molecular weight kappa carrageenans described herein have reduced the gelling temperature from about 28° C. (kappa carrageenan having 5.4% sodium, 0.09% calcium, 0% potassium by weight of the carrageenan and a viscosity of 129 cP when measured using the tests herein) to about 21° C. (kappa carrageenan of the invention having predominantly sodium cation and a viscosity of 8 cP when measured using the tests herein). Furthermore, Applicants have found that the reduced molecular weight kappa-2 carrageenans described herein have reduced the gelling temperature from about 35° C. (kappa-2 carrageenan having 7.4% sodium, 0.15% calcium, 0.67% potassium by weight of the carrageenan and a viscosity of 41 cP when measured using the tests herein) to about 25° C. (kappa-2 carrageenan of the invention having 7.7% sodium, 0.01% calcium, 1.0% potassium by weight of the carrageenan and a viscosity of 9 cP when measured using the tests herein). The gelling temperature of the gels and gel films of this invention containing the reduced molecular weight carrageen can vary depending on the other materials and combinations of reduced molecular weight carrageenans contained in the gel and gel film (e.g., plasticizers, second film formers, bulking agents, etc.). Thus, for example, without being limited hereby, the gels of the present invention can have gelling temperatures of about 60° C. or less, 50° C. or less, 45° C. or less, 40° C. or less, 35° C. or less (at least 80%, 85%, 90%, 95% by weight iota carrageenan based on the total weight of carrageenan in the gel and containing at least 50% sodium, calcium and/or potassium cation); 60° C. or less, 50° C. or less, 40° C. or less, 30° C. or less, 28° C. or less, 25° C. or less, 21° C. or less (at least 80%, 85%, 90%, 95% by weight kappa carrageenan based on the total weight of carrageenan in the gel and containing at least 50% sodium cation); and 60° C. or less, 50° C. or less, 35° C. or less, 30° C. or less, 25° C. or less (at least 80%, 85%, 90%, 95% by weight kappa-2 carrageenan based on the total weight of carrageenan in the gel and containing at least 50% sodium cation). The sodium cation can be present in an amount of at least 75%, 85%, 90%, 95%, 95% by weight based on the total cation weight.

The reduced molecular weight carrageenan used in the present invention is generally present in a gel forming amount. Such an amount is generally 0.5% to 25%, more particularly, 0.5% to 15%, more particularly, 3.0% to 15%, by weight of all components in the gel depending on the use of the gel.

The gels and gel films of the invention are generally considered to be homogeneous and thermoreversible.

As used herein, "homogeneous" defines gels and gel films that, to the naked eye, are visually uniform and free of defects such as lumps, cracks, particles that are undissolved that should be dissolved, non-uniform distribution of insoluble particles, etc. "Fish eyes" (mixed liquid and solid states) or "gel balls" (non-uniform gel structure) would not meet the definition of "homogeneous" as used herein.

The gels and gel films of the present invention can be cast and used in a wide variety of applications as cast films or in subsequent processing.

As used herein, "thermoreversible" defines a gel and gel film that has a melting temperature. As used herein, the melting temperature is the temperature or temperature range over which the gel film softens or flows.

As used herein, the phrase "gel films" refer to a thin membrane or three dimensional network, formed from the structured carrageenan. The gel-forming composition is characterized by a gel temperature, the temperature below which the molten mass of the gel composition must be cooled to form a self-supporting structure. Optionally, a molten mass can be cast hot and allowed to cool, as well as dry to further concentrate the solids (controlled moisture removal) until a gel film is formed by the gel composition. The melt temperature of a thermoreversible gel film is higher than its gel temperature.

The homogeneous, thermoreversible gel and gel film of the present invention can optionally contain at least one of a plasticizer, a second film former, a bulking agent and a pH controlling agent. The components to be added to the gel and gel film and their amounts can vary depending on the desired use of the gel and gel film.

Examples of such a plasticizer include polyols such as glycerin, sorbitol, maltitol, lactitol, corn starch, fructose, polydextrose and polyalkylene glycols such as propylene glycol and polyethylene glycol. The amount of the plasticizer can vary depending on the use of the gel and gel film and its desired elasticity. For example, such plasticizers can generally be used in an amount of at least 5%, more preferably, at least 10%, more preferably, at least 20%, more preferably, at least 30% by weight of all the components including water in the dry gel or dry gel film if a gel and gel film having more elasticity is desired; e.g., gel films to be used to make soft capsules. For other applications, such as hard capsules, where less elastic films are desired, the plasticizer can be present in an amount of 0% to 20% by weight of all the components in the dry gel film. It is possible that the gel and gel film of the invention contain no plasticizer at all.

Examples of the second film former that can be used in the present invention include at least one of a starch, starch hydrozylate, starch derivative, cellulose gum, hydrocolloid, an alkylcellulose ether or a modified alkyl cellulose ether. Examples of the hydrocolloid include at least one of kappa, kappa-2 and iota carrageenans having a higher molecular weight than those used here (e.g., having a viscosity of 10 cP or more at 75° C. as measured in a 0.10 molar sodium chloride solution containing 1.5% by weight of the higher molecular weight carrageenan) and less than fully modified versions thereof; alginates including potassium alginate, sodium alginate, ammonium alginate and propylene glycol alginate; polymannan gums (e.g., generally less than about 1000 mPs viscosity as measured at 1 wt % in water at 25° C.) such as reduced viscosity guar gum; pullulan; gellan (including high and low-acyl gellan); dextran; pectin and combinations thereof. An example of an alkylcellulose ether that can be used in the present invention is hydroxyethylcellulose. Examples of modified alkylcellulose ethers that can be used in the present invention include hydroxypropylcellulose and hydroxypropylmethylcellulose. The carrageenan used in this invention can be the only gel and film former in the gel and gel film. When the gels of the present invention contain second film formers, the carrageenan of the invention can be present in an amount of at least 10%, at least 20%, at least 50% or at least 80% by weight of the total amount of film formers in the dry gel film.

Examples of the bulking agent include non-colloidal (vegetal sourced) cellulose, microcrystalline (vegetal sourced) cellulose, microcrystalline starch, modified and unmodified starch, starch derivatives and fractions, inulin, starch hydrozylates, sugar, corn syrup and polydextrose. As used herein and in the claims, the term "modified starch" includes such starches as hydroxypropylated starches, acid-thinned starches, and the like. Examples of modified starches that can be used in the present invention include Pure Cote™ B760, B790, B793, B795, M250 and M180, Pure-Dent™ B890 and Pure-Set™ B965, all available from Grain Processing Corporation of Muscatine, Iowa, and C AraTex™ 75701, available from Cerestar, Inc. Examples of starch hydrozylates include maltodextrin also known as dextrin. Unmodified starches such as potato starch can also contribute to the film strength when combined with the hydrocolloids within the scope of the invention. In general, modified starches are products prepared by the chemical treatment of starches, for example, acid treatment starches, enzyme treatment starches, oxidized starches, cross-bonding starches, and other starch derivatives. It is preferred that the modified starches be derivatized wherein side chains are modified with hydrophilic or hydrophobic groups to thereby form a more complicated structure with a strong interaction between side chains.

The amount of the bulking agent to be used in the present invention is generally in the amount of 0 to 20% by weight of the dry gel, but more can be used, if desired, for example, at least 20%, more preferably, at least 30% by weight of the dry gel.

Note that starch, starch derivatives and starch hydrozylates can be multifunctional. That is, in addition to being used as bulking agents, they can be used as second film formers. When such are used as bulking agents and second film formers, they are generally used in an amount of at least 10%, preferably, at least 20%, more preferably, at least 30% by weight of the dry gel depending on the application; e.g., soft capsules.

Examples of the pH controlling agent that can optionally be used in the present invention include bases such as hydroxides, carbonates, citrates and phosphates, mixtures thereof and their salts (e.g., sodium citrate). The pH controlling agent can be chosen as the source of added beneficial cations such as potassium or sodium. For some compositions, the pH controlling agent can be used to improve the stability of the gel and gel film. The amount of the pH controlling agent is generally in the amount of 0 to 4%, preferably, 0 to 2%.

The gels of the invention can also contain colorants and flavorants such as sugar, corn syrup, fructose, sucrose, aspartame, sucralose, sorbitol, mannitol, maltitol, etc, whether or not other components, such as plasticizers, bulking agents, second film formers, etc. are present. One embodiment of a gel and gel film of the invention comprises the carrageenan of the invention, flavorant and water in a high solids system; e.g., greater than 40%, 50%, 60%, 65%, 75%, 80%, 85%, 90% solids.

Dry gel film thicknesses generally used for soft capsules are in the range of 0.5 to 3.0 mm, more preferably, 0.8 to 1.2 mm.

It is possible that the gels and gel films of the present invention can contain nonthermoreversible gums. However, so as not to adversely impact the homogeneous and thermoreversible nature of the gel and gel films of the present invention, such nonthermoreversible gums should be present in an amount of less than 50% by weight of the reduced molecular weight carrageenan, preferably, less than 40%, more preferably, less than 30%. Examples of such nonthermoreversible gums include crosslinked gums such as calcium set (e.g., crosslinked) pectins and/or alginates. Calcium reactive alginates and pectins, as well as their less refined forms, are considered as thermoreversible gums in the absence of divalent cations. Other non-thermoreversible gums such as tragacanth gum contribute to the thermoreversibility of the carrageenan by absorption of water within its structure, providing the same effect as increasing the carrageenan amount without the secondary film formers. Additional film formers, such as polymannans can form continuous networks, either by themselves or synergistically with other components during the activation and casting process.

The reduced molecular weight carrageenan gels of the present invention are generally made from a process utilizing an apparatus that enables sufficiently high shear, temperature (above the gelling temperature) and residence time so as to provide a homogeneous molten mass of the composition and formation of the gel upon cooling. Such apparatus include but are not limited to Ross mixers, Stephan processors, conventional jet cookers, extruders and the fluid mixing apparatus as set forth in FIG. 3. Ross mixers, Stephan processors, extruders and conventional jet cookers are readily available commercially. Prior to cooling, the molten mass can be fed to at least one of a pump, mixer or devolatilizer. An example of a device that performs any one of such functions is an extruder. An extruded molten mass can also be directed to a film forming or shaping device (e.g. spreader box, as used in a capsule forming machine) that aids in the uniform casting of a continuous film, or, through a die that allows a direct formation of a film or shaped extrudate from the molten mass delivery equipment. Care must be taken to maintain the molten mass above the initiation of restricted flow/gel structure formation. Insulated and pre-heated (to maintain proper temperatures) transfer hoses may be used to insure molten mass flow until desired gel and gel film formation is initiated on the casting rolls or at other film formation points, such as an extruder (restrictive flow, film forming device) or die. Additional processing methods (such as pre-heating the discharge/plunger-like head as seen in a Ross process system) can force (by pressure) the molten mass through the transfer hoses mentioned above. Additional insulation can help maintain molten mass temperatures through the use of a Teflon disk initially placed upon the molten mass surface immediately after removing the mixing device. In addition, the feeder hoses can be introduced to the heat controlled molten mass feeder (casting) boxes located on a capsule machine either directly to the boxes or through an optional modification of the feeder boxes which introduces a top half enclosure/cover that helps maintain molten mass temperatures within the feeder box, reduces moisture loss, and maintains uniform (center) filling of the box during the extended process of forming films for capsules. It is understood that other methods of maintaining molten mass temperatures can be used to form films for capsules. This includes, but is not limited to, extrusion of the molten mass through dies/orifices into films that: can be immediately fed into the capsule forming apparatus, stored at temperatures that maintain proper film conditions (to form capsules) until needed, or dried to desired moisture, solids and texture levels, until needed. Such dried films have the property of re-absorbing water (water is introduced by any means) throughout its gel film matrix and can be rehydrated when needed, for example, to make soft capsules or other solid forms. Moisture is introduced to the film until a desired moisture content and strength/texture is reached that will allow the film's introduction into a capsule machine to make soft capsules.

Figure 1:
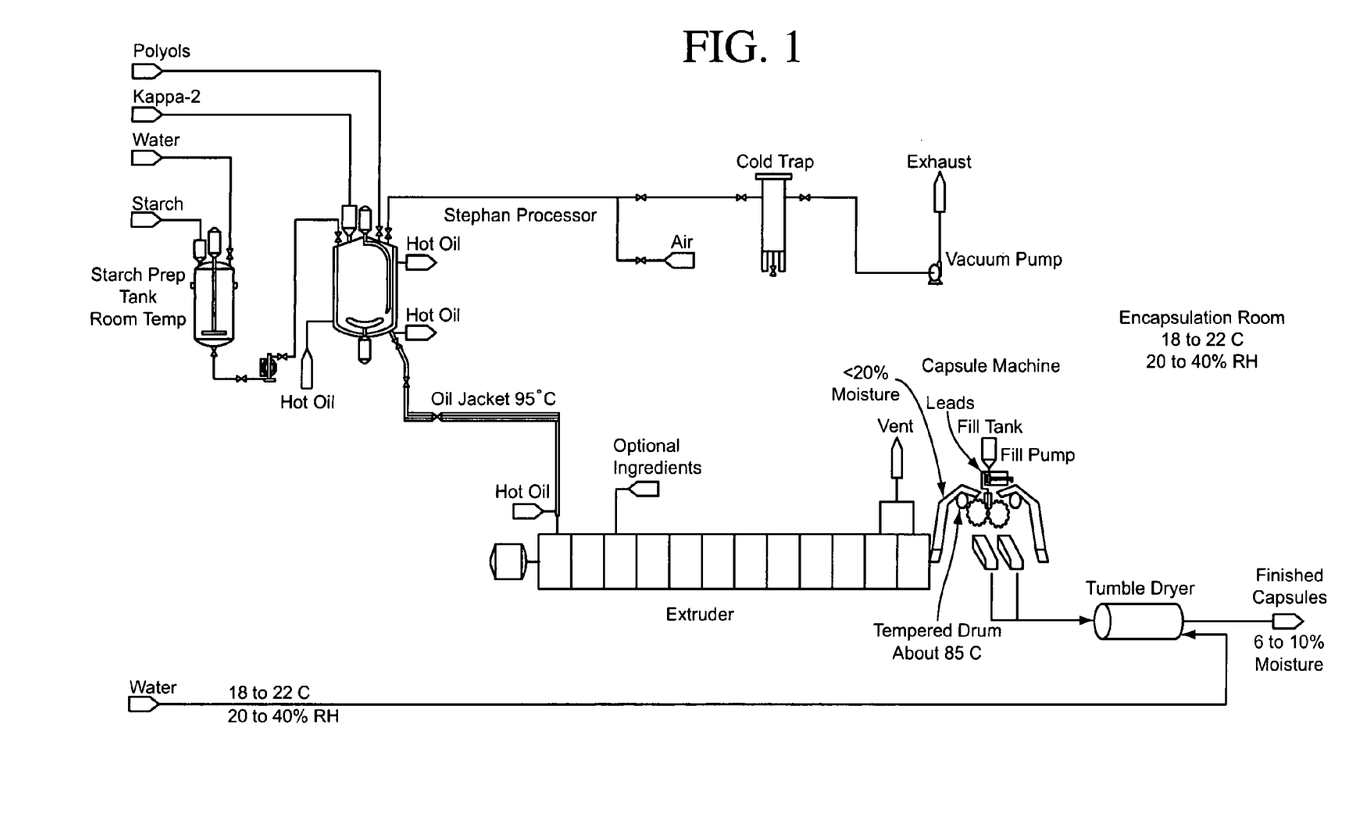
FIG. 1 is a schematic of a process of the present invention to make films and soft capsules using a Stephan processor together with an extruder.
Figure 2:
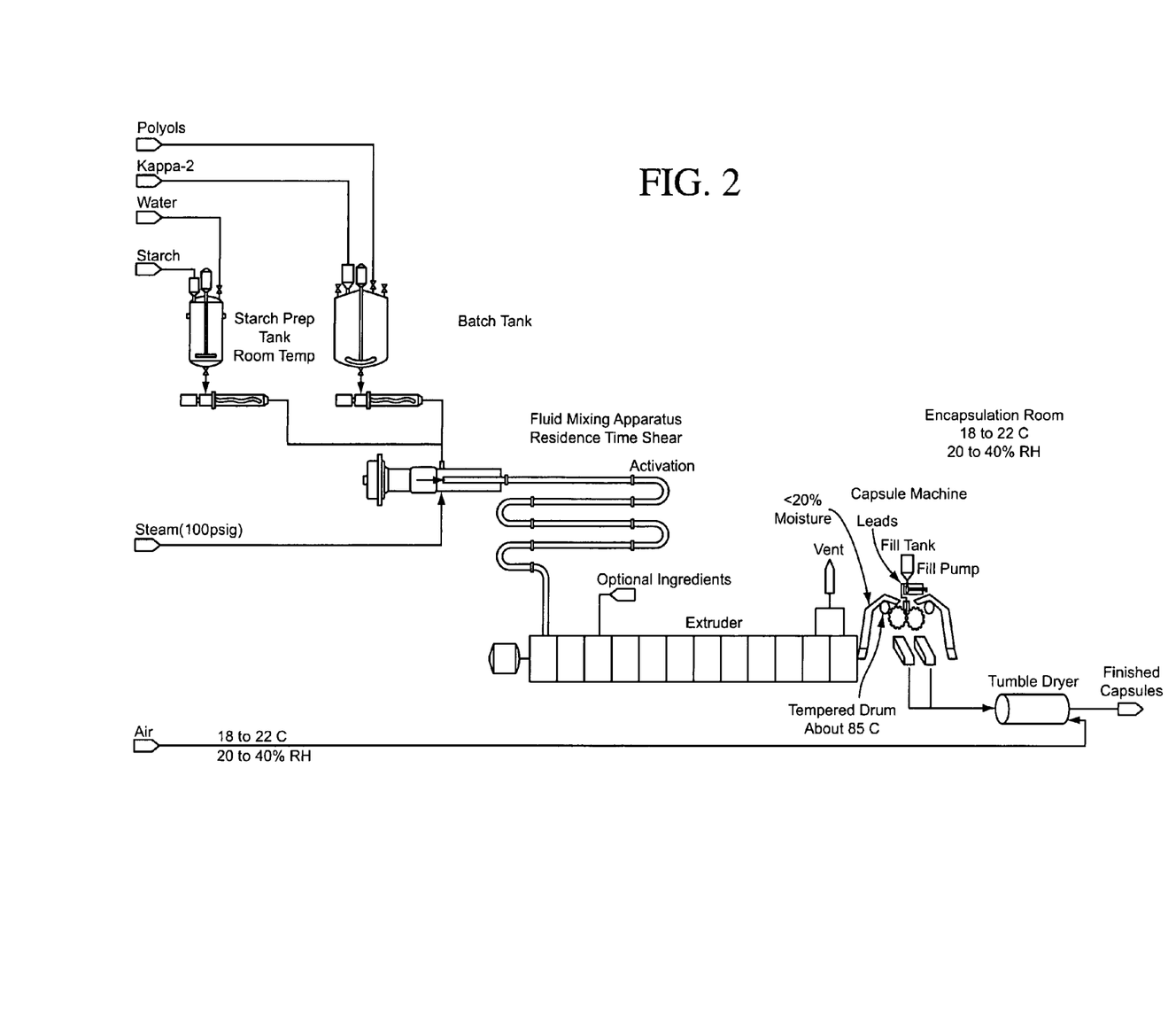
FIG. 2 is a schematic of a process of the present invention to make films and soft capsules using a fluid mixing apparatus of FIG. 3 and an extruder. The schematic shows the film coming out of the extruder proceeding to the encapsulation apparatus.
Figure 3:
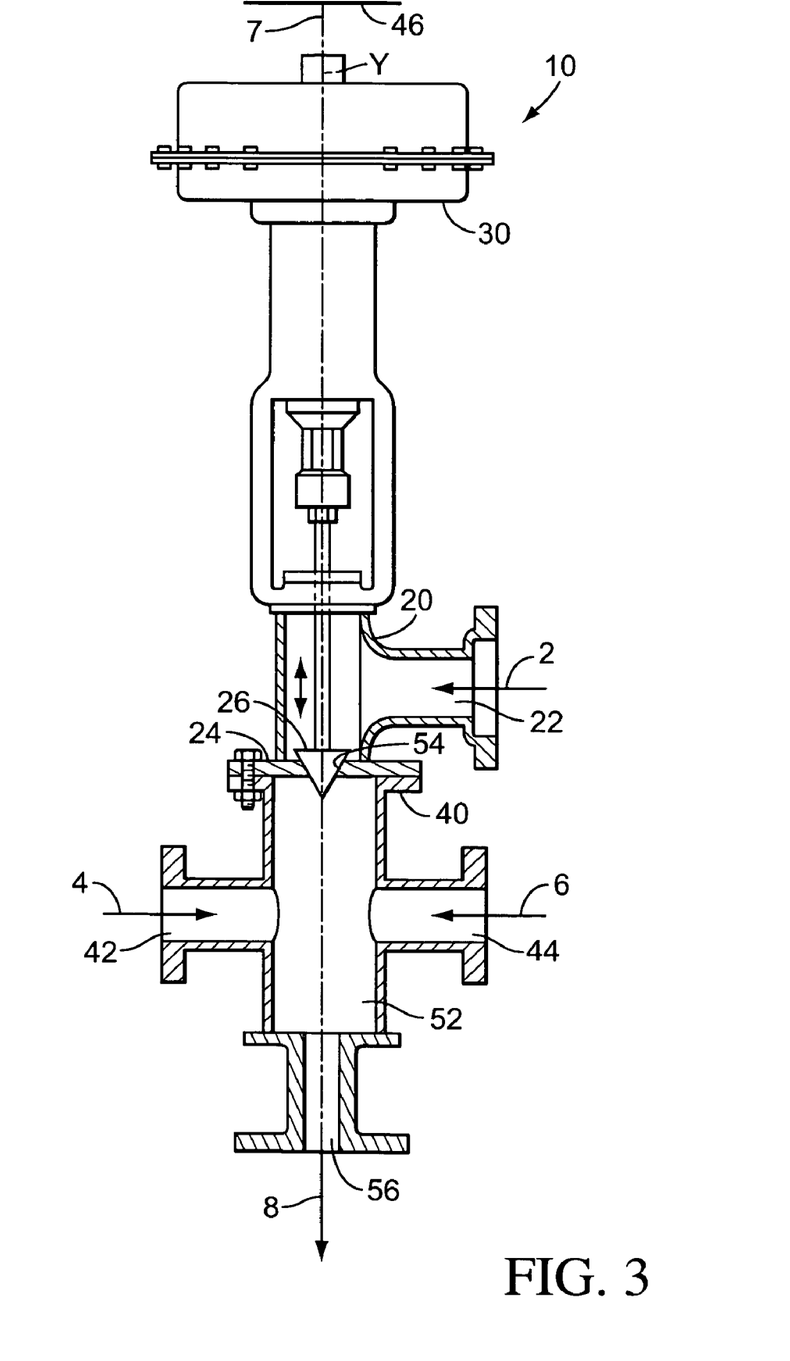
FIG. 3 is a partially broken away, side elevational view of the fluid mixing apparatus for mixing first and second fluids with steam that can be used in the process of the present invention.

As used herein, a "fluid mixing apparatus" refers to the apparatus in FIG. 3. FIG. 3 illustrates a fluid mixing apparatus 10. The fluid mixing apparatus 10 is arranged to mix steam 2 with a first fluid or slurry 4 and a second fluid or slurry 6 to produce a molten mass or slurry mixture 8.

The fluid mixing apparatus 10 comprises a first housing 20 having a first inlet 22 through which the steam 2 enters the housing 22, a nozzle end 24 from which the steam 2 exits the housing 20, and a nozzle valve or stem 26 disposed at the nozzle end 24. An actuator means 30 is connected to the first housing 20 for controlling the exit rate or exit pressure of the first fluid 2 at the nozzle end 24. The actuator means 30 may be of the type manufactured by Fisher Controls U.S.A.

The fluid mixing apparatus 10 further comprises a second, mixing housing 40 coupled to the first housing 20 at the nozzle end 24 of the first housing 20. The second housing 40 includes a second inlet 42 through which the first fluid 4 enters the second housing 40, and a third inlet 44 through which the second fluid 6 enters the second housing 40. The inlets 42 and 44 are disposed downstream of the first inlet 22. As shown in FIG. 3, the second inlet 42 and third inlet 44 are disposed in a common plane and spaced apart radially from each other, most preferably directly opposite (i.e., 180° apart) about the central axis Y of the mixing apparatus 10. The second housing 40 defines a generally cylindrical mixing chamber 52 that in turn defines a flow passage extending along the axial length of the mixing chamber 52 from an entry end 54 of the mixing chamber 52 to an exit end 56 of the chamber 52. The nozzle valve 26 is movable by the actuator 30 between seated and unseated positions at the entry end 54 to control the flow rate of steam 2 into the mixing chamber 52.

The nozzle end 24 of the first housing 20 directs the steam 2 into the entry end 54 of the mixing chamber 52. The second inlet 42 and the third inlet 44 radially direct the first fluid 4 and second fluid 6, respectively, into the mixing chamber 52. The steam 2, first fluid 4 and second fluid 6 are mixed in the mixing chamber 52 to form a molten mass or mixture 8 which exits the mixing chamber 52. The molten mass 8 then may be shaped into a shaped article or formed into a film, such as by casting the mixture 8 onto a cooling drum or by passing the mixture 8 through an extruder.

Figure 4:
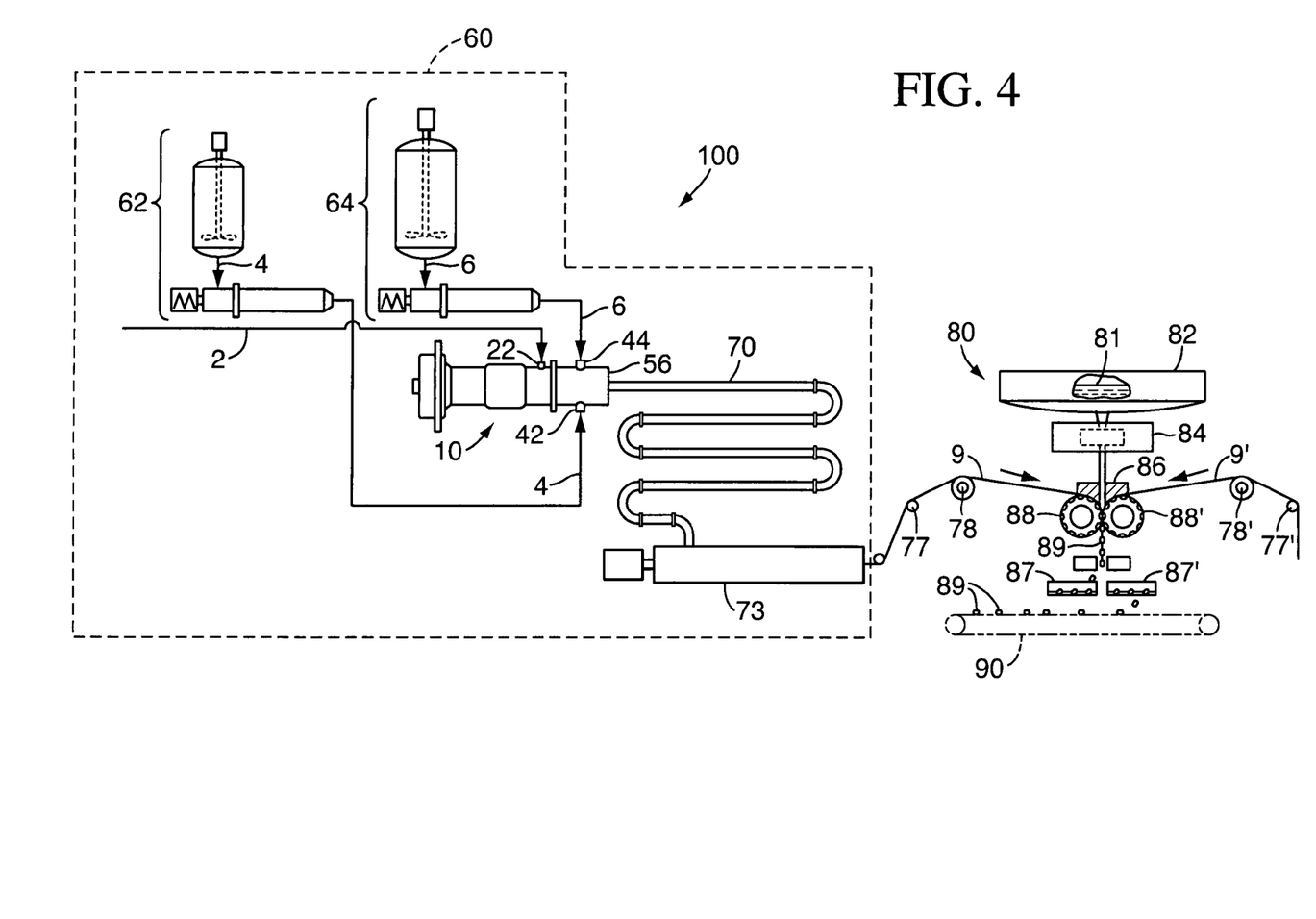
FIG. 4 is another version of the schematic of FIG. 2 showing the film coming out of the extruder proceeding to the encapsulation apparatus.

Referring next to FIG. 4, a system 100 for making films and capsules with the fluid mixing apparatus 10 includes a film preparation unit 60 for preparing and supplying a film 9, and a capsule machine 80 for forming capsules 89. The film preparation unit 60 includes: the fluid mixing apparatus 10; a first fluid supply means 62 for supplying the first fluid 4 to the fluid mixing apparatus 10; a second fluid supply means 64 for supplying the second fluid 6 to the fluid mixing apparatus 10; a slurry mixture supply path 70 for supplying the molten mass or slurry mixture 8 from the fluid mixing apparatus 8 to a shaping apparatus; an optional extruder 73 in fluid communication with the mixture supply path 70 that extrudes the mixture 8 into a film 9; a capsule machine 80 for forming capsules 89; and a conveyor belt 90 for transporting the filled capsules 90 to a subsequent process, such as drying or packaging. The extruder 73 may be of the type manufactured by Wenger or Clextrel.

The capsule machine 80 may be a conventional rotary die capsule machine of the type manufactured by R.P. Scherer Technologies of Paradise Valley, Nev. As shown in FIG. 4, the capsule machine 80 includes a capsule product storage tank 82 that holds a capsule product 81 to be encapsulated. The capsule product 81 may include liquid, semi-liquid or powder pharmaceuticals, vitamins, nutritional supplements, paint balls, pigments, agricultural actives and pre-measured food additives. The capsule machine 80 may be coupled to one or more rollers 77, 77' and 78, 78' so that the films 9, 9' may be drawn into the capsule machine 80. The film 9 is fed between heater block 86 and roller die 88. Portions of the film 9 are drawn by vacuum into recesses formed in the surfaces of the rotary die 88. An amount of the capsule product 81 is delivered into the compartment formed in the film 9 by the vacuum action. Further rotary motion of the dies 88, 88' seals the films 9, 9' together in the nip between the rotary dies 88, 88'. Filled capsules 89 drop into bins 87, 87' and are presented to conveyor 90 for drying and packaging.

Figure 5:
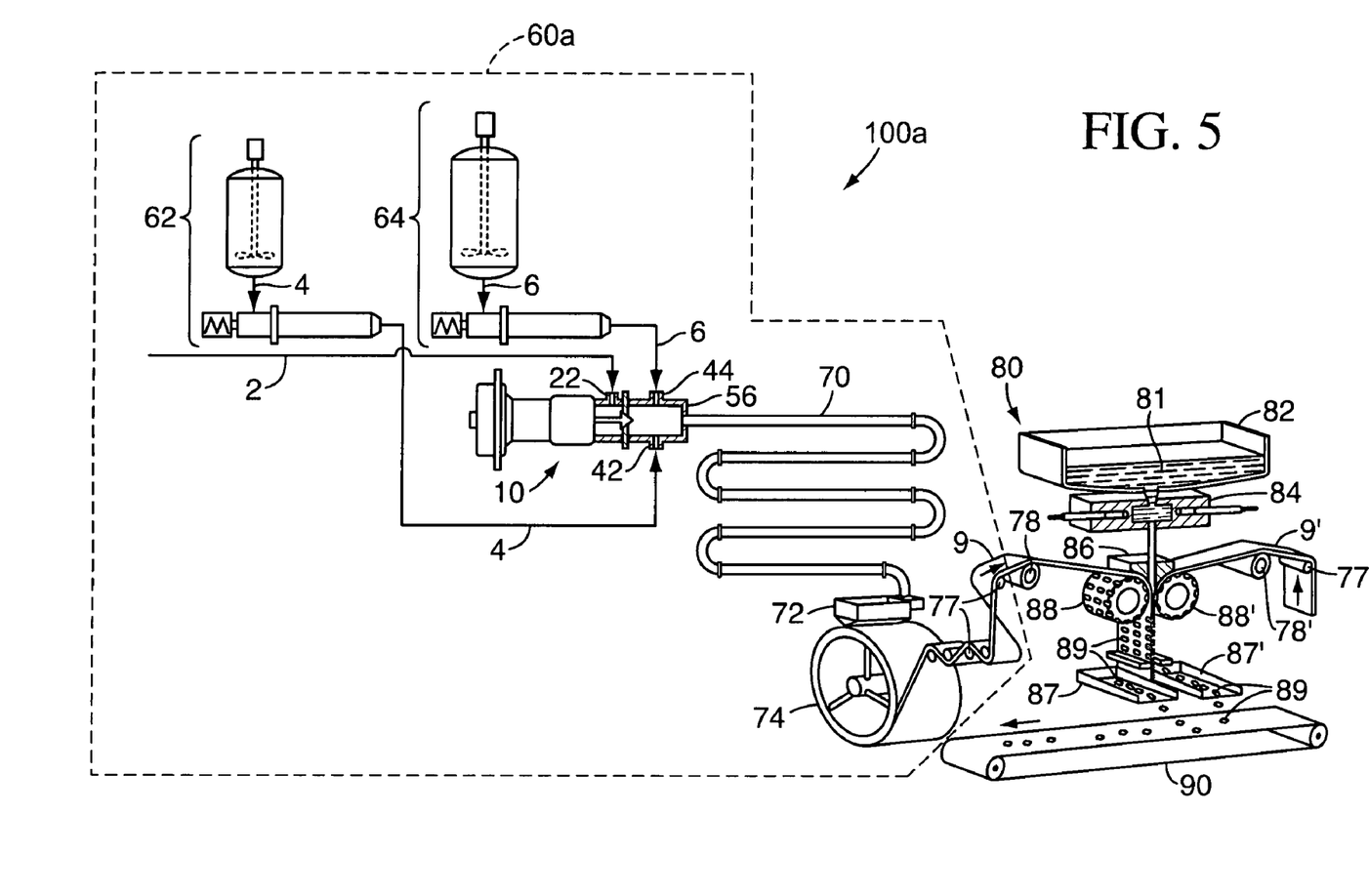
FIG. 5 is a schematic of a process of the present invention to make films and soft capsules using the fluid mixing apparatus of FIG. 3, a cooling drum and an encapsulation apparatus.

Referring next to FIG. 5, a capsule making system 100a is similar to that shown in FIG. 4, wherein like reference characters refer to like elements. In FIG. 5, however, the film preparation unit 60a includes an optional spreader box 72 and an optional cooling drum, or casting drum 74 in place of the extruder 73 of the system in FIG. 4. The system 100a includes a fluid mixing apparatus 10 and a mixture supply path 70 to direct the slurry mixture 8 away from the fluid mixing apparatus and to the spreader box 72. The spreader box 72 spreads the mixture 8 onto the casting drum 74. The film 9 is formed on the casting drum 74 as the mixture 8 cools. Thereafter, the film 9 is fed to the capsule machine 80. The film 9' preferably is formed in the same manner as the film 9 by a second film preparation unit (not shown).

The fluid mixing apparatus 10 is adapted to produce a mixture for forming a film, more particularly an edible film for making edible capsules or strips. Incompatible film components generally are placed in different fluid inlet streams so that such incompatible components come together in the first instance at the interface of the steam injection within the mixing chamber 52 of the fluid mixing apparatus. While FIG. 3 shows inlets for steam, and first and second fluids, one or more additional inlets for one or more additional fluids may be provided. Preferably, the housings 20, 40 and other components of the fluid mixing apparatus 10 are constructed of high-grade stainless steel.

As another aspect of the invention, it is noted that the molten mass need not necessarily reach homogeneity in step (i). That is, homogeneity of the molten mass can be obtained prior to or after feeding the molten composition into at least one of the mixer, pump or devolatilizer provided the molten mass reaches homogeneity prior to gelling.

The gels and gel films of the present invention have been shown from their gel strengths to be well suited to make soft capsules. Thus, the present invention is also directed to soft capsules made from the carrageenan gels and gel films of the present invention, as well as methods of making such soft capsules.

The process for making soft capsules from the reduced molecular weight carrageenan gel films of the invention includes the use of any conventional encapsulating apparatus, e.g., a conventional rotary die apparatus or concave stamping die. For example, once the molten mass of the present invention has been made, it can be cast onto drums, cooled and then fed between rotary encapsulation dies where the films are heated again, filled, sealed and cut. For a good description of this conventional process, see WO 98/42294. Alternatively, and as benefit of the present invention over conventional soft capsule processes, the use of the high shear apparatus disclosed above allows the molten mass to be sufficiently hydrated, applied to drums as they are cooling and then fed into conventional encapsulating apparatus for filling, sealing, and cutting. This continuous type process can be used to eliminate the step of having to reheat fully gelled and cooled films. The above rotary die process can be used to make soft capsules of the invention having any desired shape.

The fill materials for the soft capsules can be any materials widely used in the above rotary die process, including pharmaceutical ingredients, agricultural ingredients, nutraceutical ingredients, veterinary ingredients, foods, cosmetics, personal care, industrial, etc. and can be a liquid (including emulsions), solid, suspension, dispersion, etc.

The present invention is also directed to a solid form comprising a fill material encapsulated by the homogeneous, thermoreversible gel film of the present invention. One type of such solid form is a hard capsule. Hard capsules, as used herein, refer to those solid forms that are conventionally used, e.g., in the pharmaceutical industry whereby two half shells are formed, a fill material, usually a powder, is placed in the shells and the two halves are placed together to form the hard capsule. One process for making such hard capsules would typically involve dipping metal pins or bars into the molten composition of the present invention and allowing the gel film to form around the pins. The gel films are dried and then removed from the pins. These processes are well known in the industry as methods of making hard capsules. The fill materials for the hard capsules can be any fill materials commonly used in such dosage forms. Generally, the fill materials can be liquids (including emulsions) or solids such as powders. The fill materials can be a pharmaceutical ingredient, agricultural ingredient, nutraceutical ingredient, veterinary ingredient, food, cosmetic ingredient, etc.

The solid form may also encapsulate a powder, tablet, caplet, microcapsule or capsule in accordance with known techniques. For example, encapsulating a hard capsule with the gel film of the invention would allow for safety seal/tamper resistant capabilities.

The present invention is also directed to a delivery system comprising a homogenous, thermoreversible gel film, wherein the gel film comprises: (i) a film forming amount of the reduced molecular weight carrageenans of the invention and optionally at least one of a plasticizer, a second film former, a bulking agent, and a pH controlling agent; and (ii) an active substance. The present invention is also directed to a process for the manufacture thereof. Examples of active substances that may be contained within the gel film is at least one of an oral care agent, a breath freshening agent, an antimicrobial agent, a cooling agent, a pharmaceutical agent, a nutraceutical agent, a salivary stimulant agent, a vitamin, a mineral, a coloring agent, cosmetic ingredient, agricultural active, a sweetener, a flavorant, a fragrance or a food. Examples of a flavorant include sugar, corn syrup, fructose, sucrose, aspartame, sucralose, sorbitol, mannitol, maltitol, etc, whether or not other components, such as plasticizers, bulking agents, second film formers, etc. are present. One embodiment of a delivery system of the invention comprises the carrageenan disclosed herein, flavorant and water in a high solids system; e.g., greater than 40%, 50%, 60%, 65%, 75%, 80%, 85%, 90% solids.

The gel film can also be used to modify the dissolution profile of the dosage forms. For example, gel films of the invention can contain added components that can create solid dosage forms having immediate release, controlled, enteric or delayed release capabilities or can be released upon activation by a known event, condition or process. Definitions of "immediate release", "delayed release" and "enteric" can be found in the U.S. Pharmacopeia and are incorporated herein by reference.

The present invention is now described in more detail by reference to the following examples, but it should be understood that the invention is not construed as being limited thereto. Unless otherwise indicated herein, all parts, percents, ratios and the like are by weight.

EXAMPLES

Example 1

Iota, kappa and kappa-2 carrageenans of varying viscosities were measured at 75° C. using a Brookfield LVF viscometer and a test sample prepared at 1.5 wt % carrageenan in a 0.10 molar aqueous sodium chloride solution. The measurements are found in Table 1.

TABLE 1

Carrageenan Properties

|  | Iota | Iota | Kappa | Kappa-2 | Kappa-2 | Kappa-2 |
|---|---|---|---|---|---|---|
| Viscosity, cP | 6 | 23 | 7.5 | 9 | 20 | 41 |
| pH | 8.9 | 8.9 | 9.2 | 8.7 | 9.6 | 10.1 |
| Sodium, % | 7.47 | 7.82 | 4.80 | 7.70 | 6.90 | 7.40 |
| Potassium, % | 0.5 | 0.00 | 1.40 | 1.0 | 0.00 | 0.67 |
| Calcium, % | 0.00 | 0.00 | 0.00 | 0.01 | 0.16 | 0.15 |
| Magnesium, % | 0.00 | 0.02 | 0.03 | 0.00 | 0.03 | 0.05 |

The following procedure was used to prepare 2.25% kappa-2 carrageenan samples of varying molecular weight as indicated by viscosity where viscosity was measured at 75° C. for a 1.5% solids aqueous solution: 105 grams of water and 147 grams of corn syrup were mixed in a beaker. A dry premix of kappa-2 carrageenan, granulated sugar and salts (as indicated in Table 2) was added to the liquid and heated with agitation to 95° C. The hot liquid was poured into 2 gel dishes and 2 test tubes (½ full). The gel dishes and one test tube (positioned to obtain a gel surface at 45 degrees for use in measuring the melt temperature) were placed in a water bath at 10° C. for an hour. The second test tube was used to measure the gel temperature. The as-cast solids were approximately 62%. Break force (based on maximum force) and penetration (distance of plunger travel at maximum force) were measured on the gels using a Texture Analyzer. The gel temperatures and melt temperatures were decreased as the molecular weight (as measured by viscosity) was lowered. In particular, sample 1a which contained the kappa-2 carrageenan with viscosity of 9 cP provided a gel film with a decreased gel temperature of 25° C. and a melt temperature of 36° C.

TABLE 2

Kappa 2 (K2) Carrageenan Formulations and Properties

|  | 1a | 2a | 3a |
|---|---|---|---|
| Ingredient (g) | | | |
| K2 (9 cP) | 7.88 | 0 | 0 |
| K2 (20 cP) | 0 | 7.88 | 0 |

TABLE 2-continued

Kappa 2 (K2) Carrageenan Formulations and Properties

|  | 1a | 2a | 3a |
|---|---|---|---|
| K2 (41 cP) | 0 | 0 | 7.88 |
| Sugar | 90.13 | 90.13 | 90.13 |
| CaCl2 | 0 | 0 | 0.0 |
| KCl | 0 | 0 | 0.0 |
| As Cast | | | |
| BF (g) | 36 | 613 | 90 |
| Penetration | 32 | 33 | 41 |
| Melt temp. ° C. | 36 | 39.5 | 42 |
| Gel temp. ° C. | 25 | 35.5 | 34-36 |

The same procedure was used to prepare 2.25% iota carrageenan or kappa carrageenan samples.

TABLE 3

Iota Carrageenan and Kappa Carrageenan Formulations and Properties

|  | 3a | S 1 | 3b | S 2 | 3c | S-3 |
|---|---|---|---|---|---|---|
| Ingredient (g) | | | | | | |
| Iota (6 cP) | 7.88 | 0 | 7.88 | 0 | 0 | 0 |
| Iota (23 cP) Comp. Ex. | 0 | 7.88 | 0 | 7.88 | 0 | 0 |
| Kappa (8 cP) | 0 | 0 | 0 | 0 | 7.88 | 0 |
| Kappa (129 cP) Comp. Ex. | 0 | 0 | 0 | 0 | 0 | 7.88 |
| Sugar | 90.13 | 90.13 | 89.25 | 89.25 | 90.13 | 90.13 |
| CaCl2 | 0 | 0 | 0.38 | 0.38 | 0 | 0 |
| KCl | 0 | 0 | 0.50 | 0.50 | 0 | 0 |
| As Cast | | | | | | |
| BF (g) | 41 | 478 | 39 | 560 | 22.1 | 68 |
| Penetration, mm | 35.1 | 38 | 34.5 | 32 | 33.8 | 43.8 |
| Melt temp. ° C. | 42-43 | 66-67.5 | 58-59 | 86-88 | 23.5 | 47 |
| Gel temp. ° C. | 30-31 | 59-61 | 34-36 | 80-82 | 20-21 | 27-28 |

Example 2

The following procedures were used to prepare and evaluate the materials and films in this example. The Stephan UMC5 processor is a laboratory-scale mixing device which provided suitable high shear mixing, heating, and de-aerating of the formulations which were cast as films in the laboratory. A suitable batch size used with the Stephan UMC5 processor was 1500 grams.

An aqueous starch dispersion was prepared by dissolving any salts/buffers and pH modifiers in deionized water. The starch and/or maltodextrin (M100) were added and mixed until dissolved/dispersed.

A mixture was prepared in the Stephan UMC5 processor by premixing the plasticizers until uniform, and adding the dry carrageenans of the invention portion-wise while mixing for about 30 seconds at 200 rpm. Sorbitol Special and glycerin were used as plasticizers. Sorbitol Special is an aqueous solution of sorbitol and sorbitol anhydrides at 76% solids supplied by SPI Polyols, Inc (New Castle, Del.).

The starch dispersion was added to the non-aqueous carrageenan mixture and mixed at 300 rpm for 5 minutes. The mechanical agitation was increased to 2100 rpm and the mixture was heated to 85° C. to 95° C. with mixing. When the target temperature was achieved, the mixture was stirred for 30 minutes, then the sample was held under vacuum (50-60 bars) with continued agitation for an additional 45 minutes.

When the hold time under vacuum at temperature has been completed, the sample was poured into a preheated wide mouth quart Mason jar. Temperature and pH were recorded. Viscosity was measured on the hot sample using a Brookfield LVF viscometer.

A small portion of the sample was set aside and refrigerated usually overnight prior to measurement of gel/melt properties and solids using an Atago E series hand held refractometer (Gardco, Pompano Beach, Fla.). The melt temperature was determined by placing a small chunk of the refrigerated gel on a wire string stand held within a test tube so that the chunk does not contact the wall of the test tube. The test tube was covered with aluminum foil with a small hole to allow measurement of the gel temperature using a digital Tempermeter probe. The test tube was immersed in the heating bath so that the chunk is below the surface of a hot water bath at approximately 100° C. The melt temperature was recorded when the gelled sample became wet in appearance, softened and could be stirred (a temperature range was noted). Once the sample had melted, the test tube was transferred to a second beaker containing cold tap water (15° C.). The temperature probe was used to record the temperature as the sample was cooled and to probe the sample surface to determine whether the sample had begun to gel. The gel temperature was the temperature upon cooling where the sample no longer flowed to fill in an indentation made by the probe.

The hot sample was then cast, using a draw down bar with a gap set to give a clearance of 3 mm, onto 177 mm by 177 mm by 5 mm metal plates which were pre-sprayed with lecithin to facilitate easy removal of film material. The gel-coated plates were covered to avoid loss of moisture from the cast film. Cast films were typically refrigerated (less than 8° C.) for at least one-half hour prior to removal of the film for testing. Refrigeration is not required for film formation. Dried film strips were prepared by drying the coated plates in a 40° C. forced air/fan oven. Films dried 2 hours at 40° C. gave an intermediate solids of about 60%, while films dried overnight at 40° C. gave solids of 80% or higher. Test properties were measured at room temperature (approximately 20° C.) unless otherwise specified. The percent of solids of the dried film was determined between the cast film at its formulated solids level and the dried film by difference in weight. Break force (BF) was measured on the cast and dried film strips using a Texture Analyzer TA-108S Mini Film Test Rig.

Maltrin M100 was obtained from Grain Processing Corporation, Pure-Cote B760 was obtained from Grain Processing Corporation, Sorbitol Special was obtained from SPI Polyols and Glycerin was obtained from VWR (EP/USP grade).

TABLE 4

Properties of Kappa-2 Carrageenans Used to Make The Films

|  | Cgn X | Cgn Y | Cgn Z |
| --- | --- | --- | --- |
| Mg, % | 0.03 | 0.02 | 0.07 |
| Ca, % | 0.16 | 0.01 | 0.06 |
| K, % | 0.00 | 1.00 | 2.19 |
| Na, % | 6.90 | 7.70 | 5.12 |
| Visc, cP | 45 | 18 | 6 |
| pH | 9.6 | 8.7 | 8.1 |
| 2% water gel | | | |
| BF (g) 2% water gel (KCl) | 0 | 0 | 0 |
| BF (g) 2% water gel (KCl + CaCl$_2$) | 29 | 13 | 0 |
| BF (g) | 112 | 93 | 30 |

TABLE 5

Kappa-2 Carrageenan Films

|  | Comp Ex X1 | Comp Ex Y1 | Inventive Ex Z1 |
| --- | --- | --- | --- |
| Ingredients (g) | | | |
| Water | 834.7 | 834.7 | 825 |
| Cgn X | 75.0 | 0 | 0 |
| Cgn Y | 0 | 61.4 | 0 |
| Cgn Z | 0 | 0 | 90 |
| Calcium sulfate dihydrate | 0 | 1.7 | 0 |
| Potassium chloride | 15.0 | 0 | 0 |
| Starch B760 | 0 | 0 | 225 |
| M-100 | 227.3 | 227.3 | 0 |
| Sorbitol SP | 272.2 | 275.4 | 272.2 |
| Glycerin | 90.8 | 91.9 | 90.8 |
| Temp, ° C.* | 88 | 82 | 75 |
| Viscosity, cP* | 16,150 | 6,500 | 18,250 |
| Solids, estimated | 42 | 39 | 40 |
| Melt, ° C. | 85 | 74-77 | 62-65 |
| Gel, ° C. | 60-65 | 56 | 42 |
| pH | 6.9 | 5.8 | 6.9 |
| As Cast Film | | | |
| BF (g) at ~40% Dried 2 hrs @ 40 C. | 302 | 338 | 117 |
| BF (g) at ~60% Dried overnight 16 hours @ 40° C. | NT | 766 | 536 |
| Avg film thickness (mm) | 0.62 | — | |
| BF (g) at ~80% | 4470 | 3227 | 6073 |

NT = not tested
*Temperature and viscosity of the molten mass prior to casting

While the invention has been described in detail and with reference to specific embodiments thereof, it will be apparent to one skilled in the art that various changes and modifications can be made therein without departing from the spirit and scope thereof.

The invention claimed is:

1. A homogeneous, thermoreversible gel comprising carrageenan wherein said carrageenan has a viscosity of 5 to less than 10 cP at 75° C. when measured using a Brookfield LVF viscometer, spindle #1, at 60 r.p.m., in a 0.10 molar aqueous sodium chloride solution containing 1.5% by weight of said carrageenan based on the weight of all components in said solution, and optionally at least one of a plasticizer, a second film former, a bulking agent, and a pH controlling agent, wherein said gel has a solids content of at least 40%, said carrageenan is present in an amount of from 0.5% to 15% by weight of the gel, and said carrageenan is at least one of iota carrageenan, kappa carrageenan or kappa-2 carrageenan; and wherein (i) said carrageenan is at least 80% by weight kappa carrageenan based on the total weight of all carrageenen in the gel and the gel has a gelling temperature of 30° C. or less;

(ii) said carrageenan is at least 80% by weight kappa-2 carrageenan based on the total weight of all carrageenan in the gel and the gel has a gelling temperature of 35° C. or less; or (iii) said carrageenan is at least 80% by weight iota carrageenan based on the total weight of all carrageenan in the gel and the gel has a gelling temperature of 35° C. or less.

2. The gel of claim 1, wherein said viscosity is from 5 to 8 cP.

3. The gel of claim 1, wherein said carrageenan is the only carrageenan in the gel.

4. The gel of claim 1, wherein said gel contains a plasticizer.

5. The gel of claim 1, wherein said carrageenan contains at least one of calcium, potassium, magnesium, ammonium or sodium cation.

6. The gel of claim 5, wherein said cation is at least 75% by weight sodium based on the total cation content.

7. The gel of claim 5, wherein said cation is at least 85% by weight sodium based on the total cation content.

8. The gel of claim 5, wherein said cation is at least 90% by weight sodium based on the total cation content.

9. The gel of claim 5, wherein said cation is at least 95% by weight sodium based on the total cation content.

10. The gel of claim 5, wherein said cation is at least 98% by weight sodium or potassium or combination thereof based on the total cation content.

11. The gel of claim 1, wherein said solids content is at least 50%.

12. The gel of claim 1, wherein said solids content is at least 60%.

13. The gel of claim 1, wherein said solids content is at least 70%.

14. The gel of claim 1, wherein said solids content is at least 80%.

15. The gel of claim 1, wherein said solids content is at least 90%.

16. The gel of claim 1, wherein said carrageenan is present in an amount of at least 40% of the total dry weight of film formers in the gel.

17. The gel of claim 1, wherein said carrageenan is present in an amount of at least 80% of the total dry weight of film formers in the gel.

18. The gel of claim 1, wherein said carrageenan is the only film former present in the gel.

19. The gel of claim 1, wherein said second film former is selected from the group consisting of starch, starch derivative, starch hydrozylate, cellulose gums, alginates, propylene glycol alginate, polymannan gums, dextran, pectin, gellan, pullulan, alkylcellulose ethers, and modified alkyl cellulose ethers.

20. The gel of claim 1, wherein said plasticizer is at least one member selected from the group consisting of glycerin, sorbitol, polydextrose, maltitol, lactitol, and polyalkylene glycols; said second film former is at least one member selected from the group consisting of a starch, starch derivative, starch hydrozylate, cellulose gum, hydrocolloid, an alkylcellulose ether and a modified alkyl cellulose ether; and said bulking agent is at least one member selected from the group consisting of microcrystalline cellulose, microcrystalline starch, starch, starch derivatives, inulin, starch hydrozylates and polydextrose.

21. The gel in any of claims 1, 2-10 and 11-20, wherein said gel is a gel film.

22. An edible product comprising the gel in any of claims 1, 2-10 and 11-20.

23. The gel of claim 1, wherein said carrageenan is at least 80% by weight kappa carrageenan based on the total weight of all carrageenan in the gel and the gel has a gelling temperature of 28° C. or less.

24. The gel of claim 1, wherein said carrageenan is at least 80% by weight kappa-2 carrageenan based on the total weight of all carrageenan in the gel and the gel has a gelling temperature of 25° C. or less.

* * * * *